United States Patent [19]

Blackshear

[11] Patent Number: 5,972,311
[45] Date of Patent: Oct. 26, 1999

[54] METHOD OF PREVENTING DENTAL CARIES AND OTHER ORAL LESIONS

[75] Inventor: Perry J. Blackshear, Chapel Hill, N.C.

[73] Assignee: Duke University, Durham, N.C.

[21] Appl. No.: 09/013,043

[22] Filed: Jan. 26, 1998

[51] Int. Cl.⁶ ............................... A61K 7/16; A61K 7/26; A61K 35/78

[52] U.S. Cl. ............................ 424/49; 424/50; 424/58; 424/195.1

[58] Field of Search ......................................... 424/49–58

[56] References Cited

U.S. PATENT DOCUMENTS

| | | | |
|---|---|---|---|
| 3,952,092 | 4/1976 | Bowen et al. | 424/50 |
| 4,217,341 | 8/1980 | Suddick et al. | 424/48 |
| 5,240,710 | 8/1993 | Bar-Shalom et al. | |
| 5,310,542 | 5/1994 | Au et al. | |
| 5,362,480 | 11/1994 | Au et al. | |
| 5,409,902 | 4/1995 | Carson et al. | |
| 5,525,341 | 6/1996 | Walker et al. | 424/105.1 |
| 5,824,292 | 10/1998 | Carr et al. | 424/49 |
| 5,871,714 | 2/1999 | Budny | 424/49 |

FOREIGN PATENT DOCUMENTS

| | | |
|---|---|---|
| 0 481 701 | 4/1992 | European Pat. Off. |
| 481 701 A1 | 4/1992 | European Pat. Off. |
| 550 099 A1 | 7/1993 | European Pat. Off. |
| 664 111 A2 | 5/1995 | European Pat. Off. |
| 699 689 A1 | 3/1996 | European Pat. Off. |
| 2060647 | 5/1981 | United Kingdom. |

OTHER PUBLICATIONS

Overvoorde et al, "A Plasma Membrane Sucrose–binding Protein That Mediates Sucrose Uptake Shares Structural and Sequence Similarity with Seed Storage Proteins but Remains Functionally Distinct", The Journal of Biological Chemistry 272(25):15898–15904 (1997).

Careaga et al, "Large Amplitude Twisting Motions of an Interdomain Hinge: A Disulfide Trapping Study of the Galactose–Glucose Binding Protein", Biochemistry 34:3048–3055 (1995).

Overvoorde and Grimes, "Topographical Analysis of the Plasma Membrane–associated Sucrose Binding Protein from Soybean", The Journal of Biological Chemistry 269(21):15154–15161 (1994).

Chem. Abstr. 112:240325 (1989) of published patent application 08/349772 Cassels et al, 1989.

*Primary Examiner*—Shep K. Rose
*Attorney, Agent, or Firm*—Nixon & Vanderhye P.C.

[57] ABSTRACT

The present invention relates to a method of preventing caries and other sugar-dependent dental and oral lesions and to a carbohydrate binding protein-based composition suitable for use therein.

29 Claims, No Drawings

METHOD OF PREVENTING DENTAL CARIES AND OTHER ORAL LESIONS

TECHNICAL FIELD

The present invention relates to a method of preventing caries and other sugar-dependent dental and oral lesions, and to a carbohydrate-binding protein-based composition suitable for use therein.

BACKGROUND

It is widely agreed that there is a direct relationship between sugar consumption and caries. Both total sugar consumption and between meal consumption have been shown to be important factors in cary development. Sugar is also thought to be an important pathogenic determinant for other oral lesions, including dental plaque and calculus, and gingival disease.

While caries have declined in frequency in most industrialized counties during the past 20 years, about 25% of the population of even those countries continues to be at high risk for caries (J. Am. Dent. Ass. 123:68 (1992)). Numerous measures have been used to control dental caries. These include fluoride treatment (of drinking water and teeth), pit and fissure sealants, vaccines, and "substrate modification". This last category includes non-sucrose sweeteners that are purported to have a specific anti-cariogenic effect, such as xylitol, sorbitol, mannitol and glycerol. Xylitol in particular is used in dentifrices such as mouthwashes and chewing gum. However, at best, such non-sucrose sweeteners have a modest effect, since they do little to remove the sucrose and other cariogenic sugars present. The present invention, by contrast, provides for the removal of sugars from the oral cavity, thereby preventing the development of caries and various other oral lesions.

DETAILED DESCRIPTION OF THE INVENTION

The present invention relates to a method of removing sugars from the oral cavity of a mammal and to an oral hygiene composition suitable for use therein. The invention also relates to a method of preventing, or inhibiting the formation of, caries and various other oral lesions.

The oral hygiene composition of the invention includes as an essential ingredient at least one carbohydrate-binding protein, preferably a lectin or other sucrose or galactose/glucose binding protein. Lectins suitable for use include those that bind sugars with significant affinity (as determined operationally by interference with lectin binding to a test substance or interference with a lectin-induced hemaglutinin asssay (Liener et al, eds. The Lectins: Properties, Functions and Applications in Biology and Medicine. Academic Press Inc. (1986)), preferably, with high affinity and capacity. Such lectins include those generally belonging to the "glucose/mannose group" (Liener et al, eds. The Lectins: Properties, Functions and Applications in Biology and Medicine, Academic Press, Inc. (1986)) and include those having affinity for α-D-glucose and its polymers (e.g. glycogen and starch), sucrose (α-D-glucose linked to fructose), fructose, mannose, galactose, lactose and other dictary sugars. Specific examples include, but are not limited to, lectins from *Canavalia ensiformis* (ConA; jack bean), *Lens culinaris* (lentil), *Vicia faba* (fava bean), *Pisum sativum* (garden pea), *Lathyrus ochrus* lectin I (LOLI), *Lathyrus sativus* (chickling vetch), *Vicia cracca* (the common vetch), *Vicia sativa, Vicia ervilia, Onobrychis viciifolia* (the forage legume sainfoin), *Dioclea grandiflora* (plant related to the jack bean), *Lathyrus odoratus* (sweet pea), and *Lathyrus tingitanus* (Tangier pea). (See Wu et al, Adv. Exp. Med. Biol. 228:205, 810 (1988); Lis and Sharon, Ann. Rev. Biochem. 55:35 (1986); Liener et al, eds. The Lectins: Properties, Functions and Applications in Biology and Medicine. Academic Press Inc. (1986); Bourne et al, Proteins 8:365 (1990); Goldstein et al, Biochemistry 4:876 (1965); Manners and Wright, J. Chem. Soc. 4592 (1962); Goldstein et al, Bioch. Biophys. Acta 97:68 (1965); Goldstein and Hayes, Adv. Carb. Chem. Biochem. 35:127 (1978)). These lectins have documented affinities for glucose and sucrose (of primary importance in cary development). In addition, the affinities of these lectins are generally higher for the polymeric forms of glucose that are prevalent in the diet as glycogen (from animal sources) and starch (from plant sources). Thus, these lectins have the advantage that they bind to both the uncleaved precursors (glycogen and starch) as well as, and with even higher affinity than, glucose and sucrose.

Other carbohydrate-binding proteins suitable for use in the present invention include plant proteins associated with the plasma membrane and involved in the transport of carbohydrates. The plasma membrane-associated sucrose binding protein from soybean is an example (Overvoorde et al, J. Biol. Chem. 269:15154 (1994); Overvoorde et al, J. Biol. Chem. 272:15898 (1997)). Further carbohydrate-binding proteins appropriate for use in the invention include those described by Sauer et al (EMBO J. 9:3045 (1990)), Riesmeier et al (EMBO J. 11:4705 (1992)) and Sauer et al (Plant J. 4:601 (1993)). Also suitable for use in the present invention are bacterial galactose-glucose binding proteins, for example, the galactose-glucose binding protein from *E. coli* (Careaga et al, Biochemistry 34:3048 (1995)).

It will be appreciated from a reading of this application that the referenced carbohydrate-binding proteins can be modified by mutating their encoding sequences. The mutant protein can be expressed in an appropriate expression system (eg, a procaryotic (eg *E. coli*) or eucaryotic (eg yeast or insect cells after baculovirus infection) expression system). In this way, the affinity of a given carbohydrate-binding protein for a given carbohydrate can be modified. The affinity can be to some extent predicted theoretically, but can readily be measured empirically.

In the oral hygiene composition of the invention, the carbohydrate-binding protein, or mixture thereof (e.g., one lectin for glycogen and starch, another for sucrose, and another carbohydrate-binding protein for glucose, for example, in empirically determined ratios), can be formulated with a substantially nontoxic carrier (that is, a carrier suitable for use in the oral cavity of a mammal, particularly, a human), the product taking the form of a mouthwash, mouth rinse, tooth powder, toothpaste or tooth gel, chewing gum, or other dentifrice that can be readily removed from the mouth and discarded after use. Ingredients, other than carbohydrate-binding protein, typically found in mouth washes and rinses, tooth powders, pastes and gels, and chewing gums can be used in the preparation of the composition of the invention and routine preparative methodologies can be employed (see, for example, U.S. Pat. No. 5,362,480).

The carbohydrate-binding protein is present in the instant composition in an amount sufficient to remove sugars present in the mouth. The amount can vary, for example, with the sugar to be bound, the carbohydrate binding protein or proteins used, and the form of the composition (eg chewing gum versus mouthwash), as well as other factors. Optimum concentrations can be established readily by one skilled in the art, for example, by quantification of the sugar associated with the composition following use (eg the sucrose associated with chewing gum).

The composition of the invention can be used at any time to remove oral sugars; however, use shortly after meals, or after consumption of sugar-containing beverages or snacks, may be particularly advantageous. The length of time of use can be at the individual's convenience and as typical for the form taken by the composition.

While the invention is directed at human use, it will be appreciated that veterinary use is also contemplated. Obviously, acceptable forms of the composition may be more restricted when use in non-human animals is involved.

As indicated above, prevention of, or inhibition of development of, caries is a principle focus of the invention. It will be appreciated, however, that any oral lesion having sugar as a pathogenic determinant is susceptible to prevention or inhibition of formation/development in accordance with the invention. Such lesions include dental plaque, calculus and gingival disease. Compositions suitable for use in connection with these lesions can be formulated and used as described above.

All documents cited above are hereby incorporated in their entirety by reference.

One skilled in the art will appreciate from a reading of this disclosure that various changes in form and detail can be made without departing from the true scope of the invention.

What is claimed is:

1. A composition comprising a carrier acceptable for oral use in a mammal and a carbohydrate-binding protein selected from the group consisting of: i) a lectin having a significant affinity for α-D-glucose and polymers thereof, sucrose, fructose, mannose, galactose or lactose, and being derivable from *Lens culinaris, Vicia faba, Pisum sativum, Lathyrus ochrus, Lathyrus sativus, Vicia cracca, Vicia sativa, Vicia ervilia, Onobrychis viciifolia, Dioclea grandiflora, Lathyrus odoratus* or *Lathyrus tingitanus*, ii) a plant plasma membrane-associated sucrose binding protein, and iii) a bacterial galactose-glucose binding protein.

2. The composition according to claim 1 wherein said carbohydrate-binding protein is said lectin.

3. The composition according to claim 2 wherein said lectin is of the mannose/glucose group.

4. The composition according to claim 1 wherein said carbohydrate-binding protein is said plant plasma membrane-associated sucrose binding protein.

5. The composition according to claim 1 wherein said carbohydrate binding protein is said bacterial galactose-glucose binding protein.

6. The composition according to claim 1 wherein the composition is in the form of a toothpaste, mouthwash, mouth rinse, toothpowder, tooth gel, or chewing gum.

7. A method of reducing the amount of sugar in the oral cavity of a mammal comprising:
   i) contacting an effective amount of the composition of claim 1 with said oral cavity for a time sufficent for said carbohydrate-binding protein to bind said sugar, and
   ii) removing said composition resulting from step (i) from said oral cavity.

8. A method of preventing dental caries in a mammal, or inhibiting the formation thereof, comprising:
   i) contacting the oral cavity of said mammal with an effective amount of the composition according to claim 1 so that said carbohydrate-binding protein binds to sugar in the oral cavity of said mammal, and
   ii) removing said composition resulting from step (i) from said oral cavity,
   said prevention or inhibition thereby being effected.

9. A method of preventing, or inhibiting the development of, an oral lesion for which sugar is a pathogenic determinant, comprising:
   i) contacting the oral cavity of a mammal in need of such prevention or inhibition, with an effective amount of the composition according to claim 1 so that said carbohydrate-binding protein binds to sugar in the oral cavity of said mammal, and
   ii) removing said composition resulting from step (i) from said oral cavity,
   said prevention or inhibition thereby being effected.

10. The method according to claim 6 wherein the oral lesion is calculus or gingivitis.

11. The composition of claim 2 wherein said lectin is specific for glycogen or starch.

12. The method according to claim 7 wherein said carbohydrate-binding protein is said lectin.

13. The method according to claim 12 wherein said lectin is specific for glycogen or starch.

14. The method according to claim 12 wherein said lectin is of the mannose/glucose group.

15. The method according to claim 7 wherein said carbohydrate-binding protein is said plant plasma membrane-associated sucrose binding protein.

16. The method according to claim 7 wherein said carbohydrate-binding protein is said bacterial galactose-glucose binding protein.

17. The method according to claim 7 wherein the composition is in the form of a toothpaste, mouthwash, mouth rinse, toothpowder, tooth gel, or chewing gum.

18. The method according to claim 8 wherein said carbohydrate-binding protein is said lectin.

19. The method according to claim 18 wherein said lectin is specific for glycogen or glucose.

20. The method according to claim 18 wherein said lectin is of the mannose/glucose group.

21. The method according to claim 8 wherein said carbohydrate-binding protein is a plant plasma membrane-associated sucrose binding protein.

22. The method according to claim 8 wherein said carbohydrate-binding protein is a bacterial galactose-glucose binding protein.

23. The method according to claim 8 wherein the composition is in the form of a toothpaste, mouthwash, mouth rinse, toothpowder, tooth gel, or chewing gum.

24. The method according to claim 9 wherein said carbohydrate-binding protein is said lectin.

25. The method according to claim 24 wherein said lectin is specific for glucose or glycogen.

26. The method according to claim 24 wherein said lectin is of the mannose/glucose group.

27. The method according to claim 9 wherein said carbohydrate-binding protein is a plant plasma membrane-associated sucrose binding protein.

28. The method according to claim 9 wherein said carbohydrate-binding protein is said bacterial galactose-glucose binding protein.

29. The method according to claim 9 wherein the composition is in the form of a toothpaste, mouthwash, mouth rinse, toothpowder, tooth gel, or chewing gum.

* * * * *